US00PP15510P2

(12) United States Plant Patent
Pieters

(10) Patent No.: US PP15,510 P2
(45) Date of Patent: Feb. 1, 2005

(54) ***CHRYSANTHEMUM* PLANT NAMED 'SERCIA'**

(50) Latin Name: *Chrysanthemum×morifolium*
Varietal Denomination: Sercia

(75) Inventor: Luc Remi Johan Pieters, Staden-Oostnieuwkerke (BE)

(73) Assignee: Pieters Joseph & Luc B.V. BA, Staden-Oostnieuwkerke (BE)

( * ) Notice: Subject to any disclaimer, the term of this patent is extended or adjusted under 35 U.S.C. 154(b) by 24 days.

(21) Appl. No.: 10/783,351

(22) Filed: Feb. 21, 2004

(51) Int. Cl.[7] ..... A01H 5/00
(52) U.S. Cl. ..... Plt./294
(58) Field of Search ..... Plt./294

*Primary Examiner*—Anne Marie Grunberg
(74) *Attorney, Agent, or Firm*—C. A. Whealy

(57) ABSTRACT

A new and distinct cultivar of *Chrysanthemum* plant named 'Sercia', characterized by its upright and rounded growth habit; freely branching growth habit; uniform and freely flowering habit; daisy-type inflorescences without white-colored ray florets and yellow-colored disc florets; and excellent garden performance.

1 Drawing Sheet

Botanical classification/cultivar designation: *Chrysanthemum×morifolium* cultivar Sercia.

BACKGROUND OF THE INVENTION

The present invention relates to a new and distinct cultivar of *Chrysanthemum* plant, botanically known as *Chrysanthemum×morifolium* and referred to by the name 'Sercia'.

The new *Chrysanthemum* is the product of a planned breeding program conducted by the Inventor in Staden-Oostnieuwkerke, Belgium. The objective of the breeding program is to develop new garden *Chrysanthemums* with a flowering date of mid-September, unique inflorescence forms, attractive ray and disc coloration and good resistance to wind and rain.

The new *Chrysanthemum* originated from a cross-pollination made by the Inventor in September, 1998, in Staden-Oostnieuwkerke, Belgium, of a proprietary selection of *Chrysanthemum×morifolium* identified as NR 631, not patented, as the female, or seed, parent with the *Chrysanthemum×morifolium* cultivar Papiro, disclosed in U.S. Plant Pat. No. 12,998, as the male, or pollen, parent. The new *Chrysanthemum* was discovered and selected by the Inventor as a single plant within the progeny of the stated cross-pollination in a controlled environment in Staden-Oostnieuwkerke, Belgium.

Asexual reproduction of the new *Chrysanthemum* by terminal cuttings in Staden-Oostnieuwkerke, Belgium has shown that the unique features of this new *Chrysanthemum* are stable and reproduced true to type in successive generations.

BRIEF SUMMARY OF THE INVENTION

The cultivar Sercia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sercia'.

These characteristics in combination distinguish 'Sercia' as a new and distinct cultivar:

1. Upright and rounded growth habit.
2. Freely branching growth habit.
3. Uniform and freely flowering habit.
4. Daisy-type inflorescences with white-colored ray florets and yellow-colored disc florets.
5. Excellent garden performance.

Plants of the new *Chrysanthemum* differ from plants of the female parent selection primarily in ray floret coloration.

Plants of the new *Chrysanthemum* can be compared to plants of the male parent, the cultivar Papiro. In side-by-side comparisons conducted in Staden-Oostnieuwkerke, Belgium, plants of the new *Chrysanthemum* differed from plants of the cultivar Papiro in the following characteristics:

1. Plants of the new *Chrysanthemum* were more rounded than plants of the cultivar Papiro.
2. Natural flowering date for plants of the new *Chrysanthemum* was about 25 days earlier than natural flowering date for plants of the cultivar Papiro.
3. Plants of the new *Chrysanthemum* had larger inflorescences than plants of the cultivar Papiro.

Plants of the new *Chrysanthemum* can also be compared to plants of the cultivar Milos, not patented. In side-by-side comparisons conducted in Staden-Oostnieuwkerke, Belgium, plants of the new *Chrysanthemum* differed from plants of the cultivar Milos in the following characteristics:

1. Natural flowering date for plants of the new *Chrysanthemum* was about 20 days earlier than natural flowering date for plants of the cultivar Milos.
2. Inflorescences of plants of the new *Chrysanthemum* had more ray florets than inflorescences of plants of the cultivar Milos.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering plant of 'Sercia'.

The photograph at the bottom of the sheet comprises a close-up view of the lower and upper surfaces of typical inflorescences (top) and typical leaves (bottom) of 'Sercia'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer and fall in Staden-Oostnieuwkerke, Belgium, under commercial practice in an outdoor nursery. During the production of the plants, day temperatures averaged 19° C. and night temperatures averaged 13° C. Plants were pinched about two weeks after planting. Plants were about four months from planting into 19-cm containers when the photographs and the description were taken.

Botanical classification: *Chrysanthemum×morifolium* cultivar Sercia.

Commercial classification: Garden *Chrysanthemum.*

Parentage:

*Female or seed parent.*—Proprietary selection of *Chrysanthemum×morifolium* identified as NR 631, not patented.

*Male or pollen parent.*—*Chrysanthemum×morifolium* cultivar Papiro, disclosed in U.S. Plant Pat. No. 12,998.

Propagation:

*Type.*—Terminal tip cuttings.

*Time to initiate roots, summer.*—About 10 days at 25° C.

*Time to initiate roots, winter.*—About 12 days at 20° C.

*Time to produce a rooted cutting, summer.*—About 14 days at 25° C.

*Time to produce a rooted cutting, winter.*—About 21 days at 20° C.

*Root description.*—Fibrous, thick and freely branching; white in color.

Plant description:

*Appearance.*—Herbaceous potted *Chrysanthemum* typically grown as a spray type. Stems upright and outwardly spreading; rounded plant habit. Freely branching with lateral branches potentially developing at every node; dense and full plants. Vigorous growth habit.

*Plant height.*—About 35 cm.

*Plant width.*—About 60 cm.

*Lateral branches.*—Length: About 27 cm. Diameter: About 2 mm. Strength: Strong, flexible. Texture: Pubescent. Color: 148B.

*Foliage description.*—Arrangement: Alternate, single. Length: About 5 to 7 cm. Width: About 2 to 4 cm. Apex: Apiculate. Base: Acute. Margin: Palmately lobed. Texture, upper and lower surfaces: Smooth, leathery. Color: Developing and fully expanded foliage, upper surface: 147A; venation, 148C. Developing and fully expanded foliage, lower surface: 147B; venation, 147C. Petiole length: About 2 cm. Petiole diameter: About 1 mm. Petiole color: 147B.

Inflorescence description:

*Appearance.*—Daisy-type composite inflorescences with ray and disc florets developing acropetally on a receptacle. Inflorescences borne on terminals and lateral branches above foliage. Slightly fragrant. Typically grown as a spray-type.

*Flowering response.*—Under natural conditions, plants flower in mid-September in Northern Europe.

*Postproduction longevity.*—Inflorescences maintain good color and substance for about four weeks in an interior environment.

*Quantity of inflorescences.*—Freely flowering, about six inflorescences develop per lateral stem; uniform inflorescence development.

*Inflorescence bud.*—Height: About 5 mm. Diameter: About 6 mm. Shape: Ovoid. Color: 146D.

*Inflorescence size.*—Diameter: About 4.5 cm. Depth (height): About 1.7 cm. Disc diameter: About 1.1 cm.

*Ray florets.*—Shape: Elliptic. Orientation: Initially upright; with development, roughly perpendicular to the peduncle. Length: About 2.5 cm. Width: About 5 mm. Apex: Rounded. Base: Attentuate; short corolla tube. Margin: Entire. Texture, upper and lower surfaces: Smooth, glabrous; satiny. Number of ray florets per inflorescence: About 70. Color: When opening, upper and lower surfaces: 155D. Fully opened, upper and lower surfaces: 155D.

*Disc florets.*—Arrangement: Massed at center of receptacle. Shape: Tubular. Apex: Five-pointed. Length: About 6 mm. Width: About 1 mm. Number of disc florets per inflorescence: About 100. Color: Immature: 145C. Mature: 12A.

*Peduncles.*—Length: About 3 cm. Diameter: About 1.5 mm. Angle: Mostly erect. Strength: Flexible. Texture: Smooth; glabrous. Color: 148B.

*Reproductive organs.*—Androecium: Present on disc florets only. Gynoecium: Present on both ray and disc florets.

*Seed/fruit.*—Seed and fruit production has not been observed.

Disease/pest resistance: Resistance to pathogens and pests common to *Chrysanthemums* has not been observed on plants grown under commercial greenhouse conditions.

Weather tolerance: Plants of the new *Chrysanthemum* have been observed to be very resistant to wind, rain and temperatures ranging from about −3 to 35° C.

It is claimed:

1. A new and distinct cultivar of *Chrysanthemum* plant named 'Sercia', as illustrated and described.

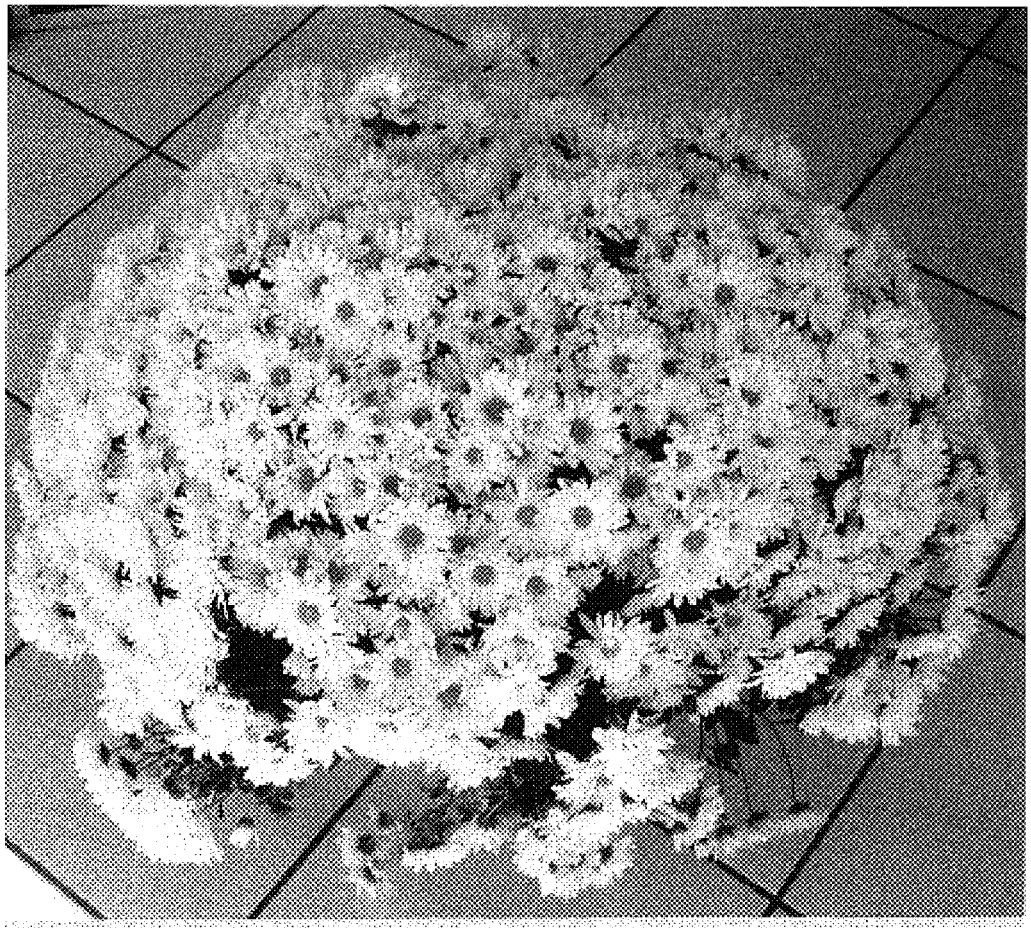
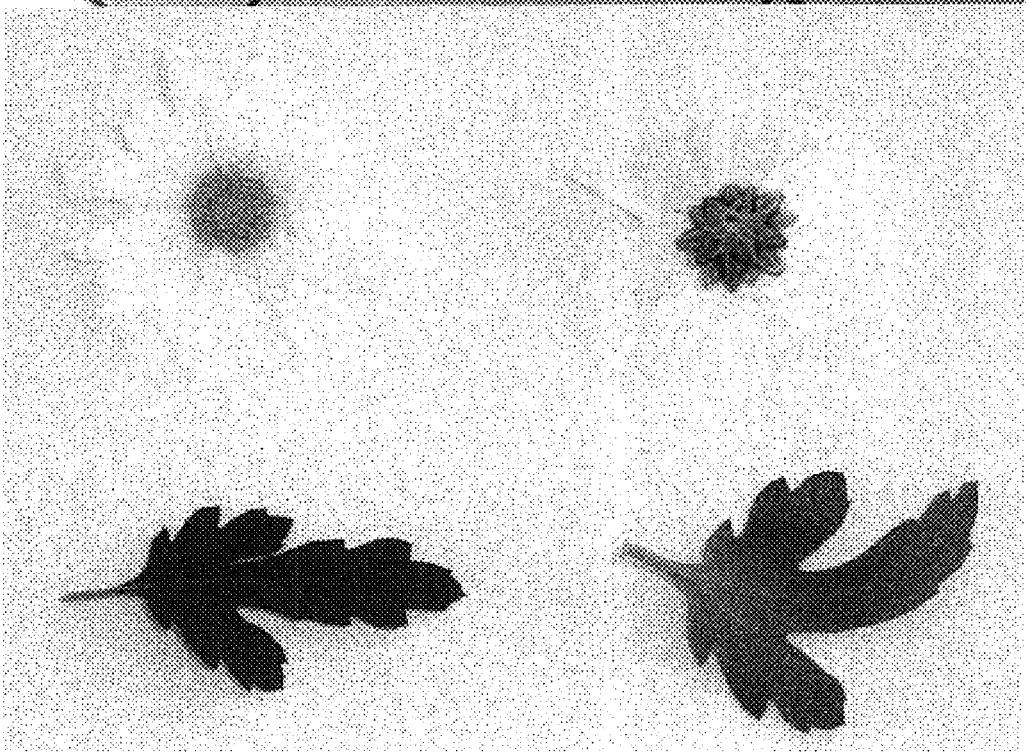

* * * * *